(12) United States Patent
Felby et al.

(10) Patent No.: US 7,598,069 B2
(45) Date of Patent: Oct. 6, 2009

(54) ENZYMATIC HYDROLYSIS OF BIOMASSES HAVING A HIGH DRY MATTER (DM) CONTENT

(75) Inventors: Claus Felby, Veksø (DK); Jan Larsen, Tommerup (DK); Henning Jørgensen, Gentofte (DK); Jakob Vibe-Pedersen, Billund (DK)

(73) Assignee: Inbicon A/S, Fredericia (DK)

( * ) Notice: Subject to any disclaimer, the term of this patent is extended or adjusted under 35 U.S.C. 154(b) by 0 days.

(21) Appl. No.: 12/102,976

(22) Filed: Apr. 15, 2008

(65) Prior Publication Data

US 2008/0182323 A1   Jul. 31, 2008

Related U.S. Application Data

(63) Continuation of application No. 11/720,079, filed as application No. PCT/IB2005/003308 on Nov. 7, 2005.

(30) Foreign Application Priority Data

Nov. 29, 2004   (DK) ............................... 2004 01854

(51) Int. Cl.
*C12N 9/42* (2006.01)
*C12P 7/10* (2006.01)

(52) U.S. Cl. ....................... 435/209; 435/165

(58) Field of Classification Search ................ None
See application file for complete search history.

(56) References Cited

U.S. PATENT DOCUMENTS

| | | | |
|---|---|---|---|
| 2,219,668 A | 10/1940 | Underkofler et al. | |
| 3,067,065 A | 12/1962 | Kusama et al. | |
| 3,212,933 A | 10/1965 | Hess et al. | |
| 4,266,981 A | 5/1981 | Tsao et al. | |
| 4,292,089 A | 9/1981 | Regnault et al. | |
| 4,304,608 A * | 12/1981 | Regnault et al. | 127/1 |
| 4,409,329 A | 10/1983 | Silver | |
| 5,185,255 A | 2/1993 | Endo et al. | |
| 5,231,017 A * | 7/1993 | Lantero et al. | 435/161 |
| 2004/0185542 A1 | 9/2004 | Yang et al. | |
| 2005/0069998 A1 | 3/2005 | Ballesteros et al. | |
| 2005/0233031 A1* | 10/2005 | Hughes | 426/52 |
| 2006/0147608 A1 | 7/2006 | Mehra et al. | |
| 2006/0233914 A1 | 10/2006 | Abbas et al. | |

FOREIGN PATENT DOCUMENTS

| | | | |
|---|---|---|---|
| WO | 8102898 A1 | 10/1981 | |
| WO | 9728306 A1 | 8/1997 | |
| WO | 9741247 A1 | 11/1997 | |
| WO | 9830710 A1 | 7/1998 | |
| WO | 02067691 A1 | 9/2002 | |
| WO | 03071025 A2 | 8/2003 | |
| WO | 03093420 A2 | 11/2003 | |
| WO | 2005118828 A1 | 12/2005 | |
| WO | 2007/009463 A1 | 1/2007 | |

OTHER PUBLICATIONS

Zuilichem et al. "Modelling of the enzymatic conversion of cracked corn by twiin-screw extrusion cooking," J. Food Engin., 1990, 12, 13-28.*
Kelsey et al. "Enhancement of cellulose accessibility and enzymatic hydrolysis by simultaneous wet milling," Biotech. & Bioeng., 1980, vol. XXII, pp. 1025-1036.*
Giovannozzi-Sermanni G et al; "Solid-state bioreactors for the sustainability" [Online 2002] Retrieved from the internet: URL:http://www.unitus.it/dipartimenti/dabac/progetti/ssbioreactors/solidstatebioreactor.htm [Retrieved on Feb. 11, 2008].
Ingesson H et al.: "The effect of shaking regime on the rate and extent of enzymatic hydrolysis of cellulose." Journal of Biotechnology, vol. 88, No. 2,, Jun. 15, 2001.
Mais U et al.: "Enhancing the enzymatic hydrolysis of cellulosic materials using simultaneous ball milling." Applied Biochemistry and Biotechnology, vol. 98-100, Apr. 2002, pp. 815-832, ISSN: 0273-2289.
Mais U et al.: "Influence of mixing regime on enzymatic saccharification of steam-exploded softwood chips." Applied Biochemistry and Biotechnology, vol. 98-100, Apr. 2002, pp. 463-472, ISSN: 0273-2289.
Lynd Lee R et al.: "Microbial cellulose utilization: fundamentals and biotechnology." Microbiology and Molecular Biology, Reviews, vol. 66, No. 3, Sep. 2002, pp. 506-577, ISSN:1092-2172.

(Continued)

*Primary Examiner*—Cecilia Tsang
*Assistant Examiner*—Christina Marchetti Bradley
(74) *Attorney, Agent, or Firm*—Budde Schou A/S; Robert C. Casad (57) ABSTRACT

Disclosed are processes for liquefaction and saccharification of polysacharide containing biomasses having high dry matter content (>20%) and preferably possessing large average particle size. The polysaccharide containing biomasses are subject to enzymatic hydrolysis in a mixer that utilizes "free fall" mixing. "Free fall" mixing provides mechanical degradation of the biomass during hydrolysis and, in the case of lignocellulosic biomass, promotes movement of cellulase enzymes along cellulose chains, which improves enzymatic hydrolysis at high dry matter.

20 Claims, 4 Drawing Sheets

OTHER PUBLICATIONS

Lynd Lee R et al.: "Biocommodity engineering." Biotechnology Progress, vol. 15, No. 5, Sep. 1999, pp. 777-793, ISSN: 8756-7938.
Gregg D et al.: "Bioconversion of lignocellulosic residue to ethanol : Process flow sheet development." Biomass and Bioenergy, vol. 9, No. 1-5, 1995, pp. 287-302, ISSN: 0961-9534.
Galbe M et al.: "A review of the production of ethanol from softwood" Applied Microbiolgy and Biotechnology, vol. 59, 2002, pp. 618-629, ISSN: 0175-7598.
Gregg D et al.: "A techno-economic assessment of the pretreatment and fractionation steps of a biomass-to-ethanol process." Applied Biochemistry and Biotechnology, vol. 57/58, 1996, pp. 711-727, ISSN 0273-2289.
Vuorinen A H: "Effect of the bulking agent on acid and alkaline phosphomonoesterase and beta-D-glucosidase activities during manure composting." Bioresource Technology, vol. 75, No. 2, Nov. 2000, pp. 133-138, ISSN: 0960-8524.
Tengborg C et al.; Enfluence of enzyme loading and physical parameters on the enzymatic hydrolysis of steam-pretreated softwood; Biotechnol. Prog. 2001; 17; p. 110-117.
Väljamäe P et al.; Mechanism of substrate inhibition in cellulose synergistic degradation; Eur. Journal of Biochem.; 268; 4520-4526; 2001.
Honda Y et al.: "Hydrolysis of lactose by immobilized beta galactosidase using a horizontal rotary column reactor." Journal of the Japanese Society for Food Science and Technology , vol. 38, No. 5, 1991, pp. 384-390. ISSN: 0029-0394. (Japanese).
Noda T et al.: "Sweet potato beta-amylase immobilized on chitosan beads and its application in the semi-continuous production of maltose" Carbohydrate Polymers, vol. 44 (Volume Date 2001), No. 3, 2000, pp. 189-195, ISSN: 0144-8617.
Varga E et al.; High solid simultaneous saccharification and fermentation of wet oxidized corn stover to ethanol; Biotechnology and Bioengineering, vol. 88, No. 5, Dec. 5, 2004; p. 567-574.
Rosgaard L et al.; Effects of substrate loading on enzymatic hydrolysis and viscosity of pretreated barley straw; Appl Biochem Biotechnol; 2007; 143:27-40.
Schutyser M A I et al.; Three-dimensional simulation of grain mixing in three different rotating drum designs for solid-state fermentation; Boitechnology and Bioengineering, vol. 79, No. 3, Aug. 5, 2002, p. 284-294.
Hardin M T et al.; Approach to designing rotating drum bioreactors for solid-state fermentation in the basis of dimensionless design factors; Biotechnology and Bioengineering, vol. 67, No. 3, Feb. 5, 2000, p. 274-282.
Felby C et al.; Ethanol from wheat straw cellulose by wet oxidation pretreatment and simultaneous saccharification and fermentation; Chapter 10; American Chemical Society, 2003; p. 157-174.
Park J-S et al.; Evaluation of operation condition and power consumption of the rotating drum type bioattritor for direct saccharification of raw starch; Kor. J. Appl. Microbiol. Biotechnol., vol. 21, No. 2, p. 157-162; 1993 (Korean).
International Search Report and Written Opinion of PCT/IB2005/003308 // WO2006/056838.
International Preliminary Report on Patentability of PCT/IB2005/003308 // WO2006/056838.
Communication pursuant to Article 94(3) EPC from the European Patent Office regarding EP application No. 95 818 844.2.
National Bioenergy Center Sugar Platform Integration Project, Biomass Program Quarterly Update #5, Oct./Dec. 2004, published Feb. 1, 2005, US Dept. of Energy, Washington DC, USA.
Abdullah, Tengerdy, and Murphy, "Optimization of Solid Substrate Fermentation of Wheat Straw", Biotechnology and Bioengineering, vol. XXVII, pp. 20-27, Jan. 1985, John Wiley & Sons, USA.
Mohaghegni, Tucker, Grohmann and Wyman, "High Solids Simultaneous Saccharification and Fermentation of Pretreated Wheat Straw to Ethanol", Applied Biochemistry and Biotechnology, vol. 33, 1002, Humana Press, USA.
Er-El, Battat, Shechter and Goldberg, "Ethanol Production from Sugar Cane Segments in a High Solids Drum Fermentor", Biotechnology Letters, vol. 3, No. 7, 385-390, 1981, Israel.
Rivard, Duff, Dickow, Eiles, Nagle, Gaddy and Clausen, "Demonstration-Scale Evaluation of a Novel High-Solids Anaerobic Digestion Process for Converting Organic Wastes to Fuel Gas and Compost", Applied Biochemistry and Biotechnology, vol. 70-72, 687-695, 1998, Humana Press, USA.
De Bari, Viola, Barisano, Cardinale, Nanna, Zimbardi, Cardinale and Braccio, "Ethanol Production at Flask and Pilot Scale from Concentrated Slurries of Steam-Exploded Aspen", Ind. Eng. Chem. Res., 41, 1745-1753, 2002, American Chemical Society, pubs.acs.org.

* cited by examiner

FIG. 1A  FIG. 1B

Longitudinal view (A) and transverse view (B) of the 5-chamber hydrolysis reactor.

FIG. 2

Concentration of glucose during liquefaction and hydrolysis of pretreated wheat straw.

FIG. 3

Concentration of glucose and ethanol during SSF of pretreated wheat straw.

FIG. 4

Concentration of glucose, xylose and ethanol during SSF of polysaccharide containing biomass.

ENZYMATIC HYDROLYSIS OF BIOMASSES HAVING A HIGH DRY MATTER (DM) CONTENT

This application is a continuation of U.S. application Ser. No. 11/720,079 filed Sep. 21, 2007 which was the national stage entry of international application PCT/IB05/03308 filed Nov. 7, 2005, which claims priority to Danish application PA 2004 01854 filed Nov. 29, 2004.

FIELD OF THE INVENTION

The present invention relates to a process for liquefaction and saccharification of biomasses containing polysaccharides, having a high dry matter content and preferably possessing fibres and particles with large average sizes. Furthermore the present invention relates to the further utilisation of such processed biomasses, e.g. for subsequent fermentation into bio-ethanol, specialty carbohydrates for food and feed as well as carbon feedstock for processing into plastics and chemicals.

BACKGROUND OF THE INVENTION

Numerous industrial and agricultural processes e.g. municipality operations, food and feed processing and forestry generate biomasses, waste and by-products containing polymeric sugars e.g. in the form of starch, cellulose and hemicellulose. Agribusiness and chemical industries as well as public organisations have considerable interest in developing processes for converting such biomasses into materials of a higher value. Thus, by way of example such biomasses could potentially be converted into bio-ethanol, biogas or chemicals using microorganisms and/or hydrolytic enzymes. However, the majority of processes known today have not yet reached large-scale commercial practice due to their high production cost and high energy demand and thus inherent uncertain economic feasibility.

Besides being important as food and feed, carbohydrates from biomass can be used as feedstock for a number of industrial processes. In the form of polymers a well-known product is paper where cellulose is the main component. However, when processed into oligomers and monomers carbohydrates are an important feedstock for a number of industrial processes. As will be described in detail they are necessary for a number of microbial processes, but in addition they can be used as feedstock for e.g. enzymatic processing into specialty carbohydrates for food and feed e.g. trehalose. Also carbohydrate oligomers and monomers may substitute petrochemicals for processing into plastics and organic chemicals. Furthermore, carbohydrates may be used as hydrogen carriers in catalytic hydrogenation.

It is therefore evident that if a low-cost and abundant resource of processed carbohydrates can be made available for industrial processing it may have a substantial economic potential.

Starch is the most widespread storage carbohydrate in plants and occurs in the form of granules, which differ markedly in size and physical characteristics from species to species. Starch granules are generally quite resistant to penetration by both water and hydrolytic enzymes due to the formation of hydrogen bonds within the same molecule and with other neighbouring molecules. However, these inter- and intra-hydrogen bonds can become weak as the temperature of the suspension is raised. When an aqueous suspension of starch is heated, the hydrogen bonds weaken, water is absorbed, and the starch granules swell. This process is commonly called gelatinization because the solution formed has a gelatinous, highly viscous consistency. Chemically, starch is a natural polymer of glucose, which is generally insoluble but dispersible in water at room temperature and made up of a repeating unit similar to that of cellulose and linked together by $\alpha$-1,4 and $\alpha$-1,6 glucosidic bonds, as opposed to the $\beta$-1,4 glucosidic bonds for cellulose. The units form either a linear chain component, called amylose, or a branched chain component, called amylopectin. Most plant seeds, grains and tubers contain about 20-25% amylose. But some, like e.g. pea starch have 60% amylose and certain species of corn have 80% amylose. Waxy varieties of grains, such as rice, are low in amylose.

Apart from starch the three major constituents in plant biomass are cellulose, hemicellulose and lignin, which are commonly referred to by the generic term lignocellulose. Polysaccharide containing biomasses as a generic term include both starch and lignocellulosic biomasses.

Cellulose, hemicellulose and lignin are present in varying amounts in different plants and in the different parts of the plant and they are intimately associated to form the structural framework of the plant.

Cellulose is a homopolysaccharide composed entirely of D-glucose linked together by $\beta$-1,4-glucosidic bonds and with a degree of polymerisation up to 10,000. The linear structure of cellulose enables the formation of both intra- and intermolecular hydrogen bonds, which results in the aggregation of cellulose chains into micro fibrils. Regions within the micro fibrils with high order are termed crystalline and less ordered regions are termed amorphous. The micro fibrils assemble into fibrils, which then form the cellulose fibres. The partly crystalline structure of cellulose along with the microfibrillar arrangement, gives cellulose high tensile strength, it makes cellulose insoluble in most solvents, and it is partly responsible for the resistance of cellulose against microbial degradation, i.e. enzymatic hydrolysis.

Hemicellulose is a complex heterogeneous polysaccharide composed of a number of monomer residues: D-glucose, D-galactose, D-mannose, D-xylose, L-arabinose, D-glucuronic acid and 4-O-methyl-D-glucuronic acid. Hemicellulose has a degree of polymerisation below 200, has side chains and may be acetylated. In softwood like fir, pine and spruce, galactoglucomannan and arabino-4-O-methyl-glucuronoxylan are the major hemicellulose fractions. In hardwood like birch, poplar, aspen or oak, 4-O-acetyl-4-methyl-glucuronoxylan and glucomannan are the main constituents of hemicellulose. Grasses like rice, wheat, oat and switch grass have hemicellulose composed of mainly glucuronoarabinoxylan.

Lignin is a complex network formed by polymerisation of phenyl propane units and it constitutes the most abundant non-polysaccharide fraction in lignocellulose. The three monomers in lignin are p-coumaryl alcohol, coniferyl alcohol and sinapyl alcohol, and they are most frequently joined through arylglyceryl-$\beta$-aryl ether bonds. Lignin is linked to hemicellulose and embeds the carbohydrates thereby offering protection against microbial and chemical degradation.

As stated above the processed biomasses could potentially be converted into bio-ethanol or chemicals using microorganisms and/or hydrolytic enzymes, or the carbohydrates from the processed biomasses could be used as feedstock for a number of industrial processes, e.g. enzymatic processing into specialty carbohydrates for food and feed or as substitutes for petrochemicals in the production of plastics and organic chemicals. In addition the processing of carbohydrates in biomass according to the present invention can be combined with separation and fractionation of the non-carbohydrate components. A particularly preferred use of a process according to the present invention is an integrated part of a process for bio-ethanol production.

Bio-ethanol production from polysaccharide containing biomasses can be divided into three steps: 1) pre-treatment, 2) hydrolysis of the polysaccharides into fermentable carbohydrates 3) and fermentation of the carbohydrates.

Pre-treatment is required if subsequent hydrolysis (e.g. enzymatic hydrolysis) of the polysaccharides requires the break down of an otherwise protecting structure (e.g. lignin) of the plant materials. Several pre-treatment techniques are known. For cereals and grains, this pre-treatment may be in the form of a simple dry milling in order to render the surfaces accessible, but for lignocellulosic biomasses thermal and/or chemical processes are needed as well. A polysaccharide containing biomass consisting of e.g. refined starch does not require said pre-treatment methods prior to enzymatic processing. Pre-treatment-processes may be based on acidic hydrolysis, steam explosion, oxidation, extraction with alkali or ethanol etc. A common feature of the pre-treatment techniques is that combined with the action of possible added reactants they take advantage of the softening and loosening of plant materials that occurs at temperatures above 100° C.

Following the pre-treatment, the next step in utilisation of polysaccharide containing biomasses for production of bio-ethanol or other biochemicals is hydrolysis of the liberated starch, cellulose and hemicellulose into fermentable sugars. If done enzymatically this requires a large number of different enzymes with different modes of action. The enzymes can be added externally or microorganisms growing on the biomass may provide them.

Cellulose is hydrolysed into glucose by the carbohydrolytic cellulases. The prevalent understanding of the cellulolytic system divides the cellulases into three classes; exo-1,4-β-D-glucanases or cellobiohydrolases (CBH) (EC 3.2.1.91), which cleave off cellobiose units from the ends of cellulose chains; endo-1,4-β-D-glucanases (EG) (EC 3.2.1.4), which hydrolyse internal β-1,4-glucosidic bonds randomly in the cellulose chain; 1,4-β-D-glucosidase (EC 3.2.1.21), which hydrolyses cellobiose to glucose and also cleaves of glucose units from cellooligosaccharides.

The different sugars in hemicellulose are liberated by the hemicellulases. The hemicellulytic system is more complex than the cellulolytic system due to the heterologous nature of hemicellulose. The system involves among others endo-1,4-β-D-xylanases (EC 3.2.1.8), which hydrolyse internal bonds in the xylan chain; 1,4-β-D-xylosidases (EC 3.2.1.37), which attack xylooligosaccharides from the non-reducing end and liberate xylose; endo-1,4-β-D-mannanases (EC 3.2.1.78), which cleave internal bonds; 1,4-β-D-mannosidases (EC 3.2.1.25), which cleave mannooligosaccharides to mannose. The side groups are removed by a number of enzymes; α-D-galactosidases (EC 3.2.1.22), α-L-arabinofuranosidases (EC 3.2.1.55), α-D-glucuronidases (EC 3.2.1.139), cinnamoyl esterases (EC 3.1.1.), acetyl xylan esterases (EC 3.1.1.6) and feruloyl esterases (EC 3.1.1.73).

The most important enzymes for use in starch hydrolysis are alpha-amylases (1,4-α-D-glucan glucanohydrolases, (EC 3.2.1.1). These are endo-acting hydrolases which cleave 1,4-α-D-glucosidic bonds and can bypass but cannot hydrolyse 1,6-alpha-D-glucosidic branchpoints. However, also exo-acting glycoamylases such as beta-amylase (EC 3.2.1.2) and pullulanase (EC 3.2.1.41) can be used for starch hydrolysis. The result of starch hydrolysis is primarily glucose, maltose, maltotriose, α-dextrin and varying amounts of oligosaccharides. When the starch-based hydrolysate is used for fermentation it can be advantageous to add proteolytic enzymes. Such enzymes may prevent flocculation of the microorganism and may generate amino acids available to the microorganism.

In combination with pre-treatment and enzymatic hydrolysis of lignocellulosic biomasses, it has been found that the use of oxidative enzymes can have a positive effect on the overall hydrolysis as well as the viability of the microorganisms employed for e.g. subsequent fermentation. The reason for this effect is the oxidative crosslinking of lignins and other phenolic inhibitors as caused by the oxidative enzymes. Typically laccase (EC 1.10.3.2) or peroxidase (EC 1.11.1.7) are employed either externally or by incorporation of a laccase gene in the applied microorganism.

Enzymatic hydrolysis of biomass has previously been described. However, in case of lignocellulosic biomasses only material consisting of fibres and particles with an average size below 1 inch (25.4 mm) and furthermore having a relatively low dry matter content, i.e. below 20% (w/w), have successfully been hydrolysed by such a method.

U.S. Pat. No. 4,409,329 describes hydrolysis of solid cellulose material to sugar, where cellulose is hydrolysed to simple sugars by treating a granular slurry of 3-20% (w/w) solid feed containing 30-80% (w/w) cellulose, with a cellulase enzyme complex. The solid cellulose-containing charge stock had a mean particle size from 0.01 to 1 inch (0.0254-25.4 mm) in diameter. Perforated rotorblades were used for mixing.

US2002117167A describes enzymatic hydrolysis of hemicellulose in biomass material, comprising solubilizing at least a portion of hemicellulose and hydrolyzing the solubilized hemicellulose to produce at least one monosaccharide. The utilised biomass is preferably aqueous slurry of raw or pre-treated material. The biomass material may be any cellulosic material that includes hemicellulose. The process is described as being especially effective with grain fibres such as corn, wheat, rice, oats or barley.

US2004005674A describes a process for enzymatic hydrolysis of lignocellulose. Degradation of lignocellulose to sugars comprises contacting the lignocellulose with at least one auxiliary enzyme and at least one cellulase. The lignocellulosic material was grounded (the average fibre size of the material was not further specified) and had a low dry matter content (0.2 g of grounded stover material in 10 ml of the enzyme solution).

SUMMARY OF THE INVENTION

The present invention relates to a process for liquefaction and saccharification of polysaccharide containing biomasses, having a relatively high dry matter content, preferably above 20%, and preferably consisting of relatively large fibres and particles preferably with a distribution of fibre and particle sizes wherein at least 20% (w/w) of the biomass ranges within 26-70 mm. Furthermore, the process is particularly suited for the liquefaction and saccharification of polysaccharide containing biomasses consisting primarily of starch, refined starch, cellulose, hemicellulose and lignin, e.g. grains or wheat straw. In the case of lignocellulosic biomasses these are preferably pre-treated by subjection to temperatures between 110-250° C. for 1-60 min. in a manner, which secures accessibility of the cellulose to the enzymes and at the same time secures a limited content of fermentation inhibitors in the pre-treated biomass. The present invention combines enzymatic hydrolysis based on the combination of hydrolytic enzymes including a carbohydrolytic enzyme and an oxidative enzyme with a type of mixing relying on the principle of gravity ensuring the application of mechanical forces, primarily shear and tear forces, to the biomasses. Preferred types of mixing are e.g. free fall mixers such as drum mixers, tumble mixers or similar mixing devices.

DESCRIPTION OF THE INVENTION

Production of concentrated sugar solutions is beneficial in relation to subsequent fermentation or other microbial processes due to improved volumetric productivity and reduced cost of down stream processing. In case of bio-ethanol production, the energy requirement for distillation is significantly reduced if the fermentation broth contains above 4% ethanol (Galbe and Zacchi, 2002). This requires a sugar concentration above 8%, which with most types of lignocellulosic biomasses corresponds to an initial dry matter content above 20%. It is in other words desirable to subject polysaccharide-containing biomasses with high dry matter contents, preferably above 20%, to enzymatic hydrolysis in order to be able to subsequently produce bio-ethanol-containing fermentation broths suitable for distillation of ethanol.

The processes of the present invention provide a degree of enzymatic hydrolysis of typically 30-50%. However, under optimised conditions even a higher degree of enzymatic hydrolysis may be obtained. The liquefied and saccharificated biomass will consequently contain relatively large amounts of glucose, xylose, cellobiose, lignin, non-degraded cellulose and hemicellulose and still active enzymes suitable for further processing i.e. fermentation processes (ethanol, lactic acid etc.). The liquefied biomass will also be suitable for gasification, hydrogenation, organic synthesis, or production of biogas and feed.

If the polysaccharide containing biomasses are lignocellulosic the pre-treatment must ensure that the structure of the lignocellulosic content is rendered more accessible to the enzymes, and at the same time the concentrations of harmful inhibitory by-products such as acetic acid, furfural and hydroxymethyl furfural remain substantially low. There are several strategies to achieve this, which all implies subjecting the lignocellulosic material to temperatures between 110-250° C. for 1-60 min e.g.:

Hot water extraction

Multi stage dilute acid hydrolysis, which removes dissolved material before inhibitory substances are formed Dilute acid hydrolyses at relatively low severity conditions Alkaline wet oxidation Steam explosion Almost any pre-treatment with subsequent detoxification Polysaccharide containing biomasses according to the present invention includes any material containing polymeric sugars e.g. in the form of starch as well as refined starch, cellulose and hemicellulose. Biomasses having a dry matter content above 20% are preferred.

Relevant types of biomasses for enzymatic hydrolysis and mixing according to the present invention may include biomasses derived from agricultural crops such as e.g.:

Starch e.g. starch containing grains and refined starch

Corn stover

Bagasse

Straw e.g. from rice, wheat, rye, oat, barley, rye, rape, sorghum

Softwood e.g. *Pinus sylvestris, Pinus radiata*

Hardwood e.g. *Salix* spp. *Eucalyptus* spp.

Tubers e.g. beet, potato

Cereals from e.g. rice, wheat, rye, oat, barley, rye, rape, sorghum and corn

Waste paper, fibre fractions from biogas processing, manure, residues from oil palm processing, municipal solid waste or the like with a similar dry matter content.

If the polysaccharide containing biomasses are lignocellulosic, the material may be cut into pieces where 20% (w/w) of the biomass preferably ranges within 26-70 mm, before pre-treatment. The pre-treated material has preferably a dry matter content above 20% before entering the mixing device. Besides liberating the carbohydrates from the biomass, the pre-treatment process sterilises and partly dissolves the biomass and at the same time washes out potassium chloride from the lignin fraction.

The mixing performed in a process according to the present invention serves at least a four-fold purpose.

Firstly, it ensures close contact between the enzymes used and the polysaccharide containing biomass (substrate), as this will in most cases be insoluble or only very slightly soluble.

Secondly, the mechanical work performed on the material during the mixing helps tearing larger biomass fibres and particles apart and will therefore assist in increasing the surface area of the material. This will increase the accessibility of e.g. cellulose and hemicellulose to the enzymes used. To further increase the mechanical work on the material, steel balls or similar means that will collide with the material might be added to the drum.

Thirdly, the mixing of the material prevents local accumulation of high cellobiose concentration that—as is well known for a person skilled in the art—can inhibit e.g. cellulase enzymes, especially the cellobiohydrolases.

Fourthly, an important characteristic of the cellulase enzymes is the influence of cellulose binding domains (CBD) on the enzyme performance. CBD's are functional parts of cellulose degrading enzymes. The CBD enables adhesion of the water-soluble enzyme onto an insoluble substrate surface (cellulose). The close association between the enzyme and cellulose provided by the CBD enhances the catalytic rate and stability of the enzyme. To hydrolyse cellulose, the enzyme must change the position of the CBD on the cellulose chain. It is believed that mechanical action, i.e. mixing, is important for the movement of the CBD and consequently for the enzymatic action of the enzymes along the cellulose chain.

In addition to the above it should be noted that enzymatic hydrolysis of biomass has traditionally been conducted in stirred tank reactors equipped with impellers (e.g. Rushton turbine or Intemig impeller) mounted on a centrally placed impeller shaft similar to what is used in the fermentation industry. Due to this equipment, solutions of high viscosity, very sticky or very dry material cannot be stirred efficiently but will result in zones with very poor or no mixing. Furthermore, stirrings of such solutions require very large energy inputs, which is detrimental to the process economy. Operating with polysaccharide containing biomasses this has previously restricted the upper possible limit to app. 20%. The gravity based mixing principle according to the present invention overcomes this problem and may be used for polysaccharide containing biomasses with a dry matter content up to 80%, preferably 20-50%. The principle of gravity mixing according to the present invention can easily be scaled up and be applied for all kinds of biomasses, besides refined starch, containing up to more than 80% cellulose.

Unlike conventional stirred tank reactors traditionally used for enzymatic hydrolysis, a gravity based mixing principle, i.e. a drum mixer, a mixer with a rotary axis lifting the biomass or similar mixing devise utilising a free fall principle, at the same time enables an efficient mixing even with small power inputs and high dry matter contents and furthermore performs a mechanical processing/degradation through the forces of gravity including shear and tear forces between material and drum as well as the forces resulting from the impact between falling material and the bottom of the drum and at the same time positively effects the influence of cellulose binding domains (CBD) on enzyme performance.

Although processing of non-miscible plant materials, such as e.g. polysaccharide containing biomass with relatively high dry matter content and large average fibre and particle size, is known from solid-state fermentation or bioreactors, where tumble type mixers are used for blending (Giovanozzi et al. 2002), this principle has not previously been implemented in a dedicated liquefaction/saccharification process or a bio-ethanol fermentation process.

The present invention provides a process for processing of biomasses at relatively high dry matter contents, e.g. dry matter contents between 20-80%, preferably between 20-50%. Furthermore, the process according to the present invention ensures efficient liquefaction and saccharification enabling the direct use of the end product in e.g. fermentors.

Enzymes capable of effecting a conversion of starch, cellulose and hemicellulose or parts thereof into glucose, xylose and cellobiose are added to the biomass either in native form or in form of microbial organisms giving rise to the accumulation of such enzymes. The pH and the temperature of the biomass are adjusted with reference to the pH-optimum and the temperature optimum of the enzymes applied.

Depending on enzyme loading, the biomass will be liquefied and saccharified to a liquid without any or only with few remaining large fibres and particles within 3-24 hours. Adding a glucose metabolising microorganism at any given time during the hydrolysis and liquefaction may enhance the degree of enzymatic hydrolysis as inhibitory enzyme products are thereby removed.

DETAILED DESCRIPTION OF THE INVENTION

A process according to the present invention can be performed using the following preferred technical parameters.

Dry matter content: 20-80%, preferably 25-70%, more preferably 25-60%, even more preferably 25-50% or 25-40% and most preferably 25-35%

Distribution of fibre and particle sizes of lignocellulosic biomass: 0-150 mm, preferably, 5-125 mm, more preferably, 10-100 mm, even more preferably 15-90 mm or 20-80 mm and most preferably 26-70 mm. The preferred distribution of fibre and particle sizes is defined as at least 20% (w/w) of the lignocellulosic biomass ranging within the preferred interval.

If the polysaccharide containing biomass is lignocellulosic, it has to be pre-treated e.g. by a hot water extraction. If a hydro thermal pre-treatment is chosen the following technical data are preferred:

Pre-treatment temperature: 110-250° C., preferably 120-240° C., more preferably 130-230° C., more preferably 140-220° C., more preferably 150-210° C., more preferably 160-200° C., even more preferably 170-200° C. or most preferably 180-200° C.

Pre-treatment time: 1-60 min, preferably 2-55 min, more preferably 3-50 min, more preferably 4-45 min, more preferably 5-40 min, more preferably 5-35 min, more preferably 5-30 min, more preferably 5-25 min, more preferably 5-20 min and most preferably 5-15 min Dry matter content after pre-treatment of at least 20 w/w %.

Enzymatic treatment of polysaccharide containing biomasses in a gravity mixer:

If a vessel based on the free fall mixing concept in the form of a reactor with a horizontal placed stirrer shaft lifting the biomass or similar mixing devise is used, the following technical data are preferred:

Rotational speed: 0-30 rpm, preferably 0-20 rpm, more preferably 0-15 rpm even more preferably 0-10 rpm and most preferably 0-5 rpm.

Rotation with periodically alternated rotating direction.

Rotation in pre-defined intervals.

The optimal rotational speed will depend on the volume of the vessel, the preferred rotational speed may thus be relatively high when the process is carried out in a relatively small vessel, while it may be relatively low when the process is carried out in a relatively large vessel.

Enzymes for Lignocellulosic Biomass:

Cellobiase (e.g.NOVOZYM 188, a liquid cellulase preparation enriched in 1,4-$\beta$-D-glucosidase)

Cellulase (e.g. CELLUCLAST 1.5 FG L, a liquid cellulase preparation)

Enzyme loading in Filter Paper Units (FPU)/g DM. 1 FPU equals the amount of enzyme necessary to hydrolyse 1 µmol/min of glycosidic bonds on Whatmann #1 filter paper, under specified conditions well known to a person skilled in the art. However, enzymatic activity could in principle be supplied in any conceivable form including through the addition of microorganisms giving rise to the desired enzymatic activity: corresponding to 0.001-15 FPU/g dry matter, preferably 0.01-10 FPU/g dry matter, more preferably 0.1-8 FPU/g dry matter, more preferably 1-7 FPU/g dry matter and most preferably less than 6 FPU/g Enzymes for starch containing biomass:

Enzymes in the processing of starch: alpha-amylases and glucoamylases

Treatment time for enzymatic hydrolysis: 0-72 hours, preferably 1-60 hours, more preferably 2-48 hours and more preferably 3-24 hours such as 4-24 hours, such as 6-24 hours, such as 8-24 hours, such as 10-24 hours, such as 12-24 hours, such as 18-24 hours or 22 hours Temperature for enzymatic hydrolysis. Adjusted with reference to the optimum temperatures of the applied enzymatic activities: 0-105° C., preferably 10-100° C., more preferably 15-90° C., more preferably 20-80° C., more preferably 25-70° C. and most preferably 30-70° C. such as 40-45° C. or room temperature.

pH of biomass. Adjusted with reference to the optimum pH of the applied enzymatic activities: 3-12, such as 5-10, such as 6-9, such as 7-8 and preferably 4-11

The enzymatic treatment can be conducted as a batch, fed batch or a continuous process.

EXAMPLE 1

Enzymatic Hydrolysis in Laboratory Scale

Pressed pre-treated wheat straw with an average size of approximately 40 mm (counter-current water extraction at 180-200° C. for 5-10 min., water and dry matter flow ratio of 5:1) corresponding to 25 g dry weight (=67.0 g pre-treated straw) was put into a plastic bag. 0.75 mL of NOVOZYM 188, a liquid cellulase preparation enriched in 1,4-β-D-glucosidase, 3.75 mL of CELLUCLAST 1.5 FG L, a liquid cellulase preparation, and 11.9 mL of 50 mM sodium citrate buffer, pH 5.0, was mixed and sprayed onto the straw. This resulted in a final dry matter content of 30%. The enzyme loading corresponded to 10 Filter Paper Units (FPU)/g DM.

The mixer consisted of a drum (1.0 m long and 0.78 m in diameter) with 5 internal ribs along the long axis to ensure proper mixing of the material. The drum rotated along the horizontal axis with a speed of 26 rpm. The mixing/hydrolysis of the material was performed for 18-24 hours at room temperature. This resulted in a thick paste without any remaining large fibres. A control bag with the same enzyme loading but no mixing showed no sign of degradation of the straw.

Part of the resulting material after the enzymatic hydrolysis for 24 hours (an amount corresponding to 29 g dry matter) was diluted to 15% dry matter in a blue cap bottle and yeast (Baker's yeast, De Danske Spritfabrikker) was added. The bottle was closed by an air lock and placed for 72 hours at 30° C. with stirring at 500 rpm. The resulting liquid contained 33 g/L of ethanol, 10 g/L of xylose. No glucose was detected indicating that the yeast was capable of utilising all glucose produced during the hydrolysis. Assuming an ethanol yield on glucose of 0.5 g ethanol per g glucose this corresponded to conversion of 70% of the originally cellulose.

EXAMPLE 2

Enzymatic Hydrolysis at Pilot Scale

Pressed pre-treated wheat straw with an average size of approximately 40 mm (pre-treated by counter-current water extraction at 180-200° C. for 5-10 min. with a water and dry matter flow ratio of 5:1) corresponding to 7 kg DW (=20 kg pre-treated straw) was put into a conventional rotary cement mixer, with a horizontal axis tilted about 10 degrees. The mixer had 2 internal ribs along the long axis to ensure mixing of the material. A lid was mounted on the opening to avoid evaporation from the mixer. The mixer drum rotated along the horizontal axis with a speed of 29 rpm.

200-1150 mL of CELLUCLAST 1.5 FG L, a liquid cellulase preparation, and 40-225 mL of NOVOZYM 188, a liquid cellulase preparation enriched in 1,4-β-D-glucosidase, were added to the straw. This resulted in a final dry matter content of 30%. The enzyme loading corresponded to 3-15 FPU/g DM. The pH was adjusted to 4.8 to 5.0 by addition of sodium carbonate.

The cement mixer was heated to 40-45° C. by use of a fan heater. The mixing/hydrolysis of the material was performed for 22 hours. Depending on enzyme loading this resulted in a more or less viscous liquid without any remaining large fibres. The pre-treated straw was degraded to a paste in app. 3-5 hours. After 5-24 hours of mixing the paste was changed to a viscous liquid. Control experiments with pre-treated wheat straw only or wheat straw pre-treated at only 160° C. but using the same enzyme loading showed no sign of liquefaction of the straw.

Simultaneous saccharification and fermentation was performed by adding yeast to the cement mixer after 24 hours of hydrolysis at 40-45° C. using an enzyme loading of 10-15 FPU/g DM. The temperature was allowed to cool to below 35° C. and compressed yeast (Baker's yeast, De Danske Spritfabrikker) was added to a concentration of approximately 1% (w/w) based on initial dry matter of straw. The saccharification and fermentation was continued for 48 hours at 25° C.

The resulting material was centrifuged for 15 min at 2500 rpm. The supernatant was filtered through a 0.45 μm filter and analysed for sugars on HPLC. At an enzyme load of 15 FPU/g DM, the supernatant contained 70 g/L of glucose, 30 g/L of xylose after 24 hours of hydrolysis. This corresponded to 50% hydrolysis of the cellulose and hemicellulose originally present in the straw. The simultaneous saccharification and fermentation using an enzyme loading of 10 FPU/g DM resulted in 42 g/L of ethanol and 30 g/L of xylose.

EXAMPLE 3

Liquefaction, Hydrolysis and Fermentation

Figure 1A:
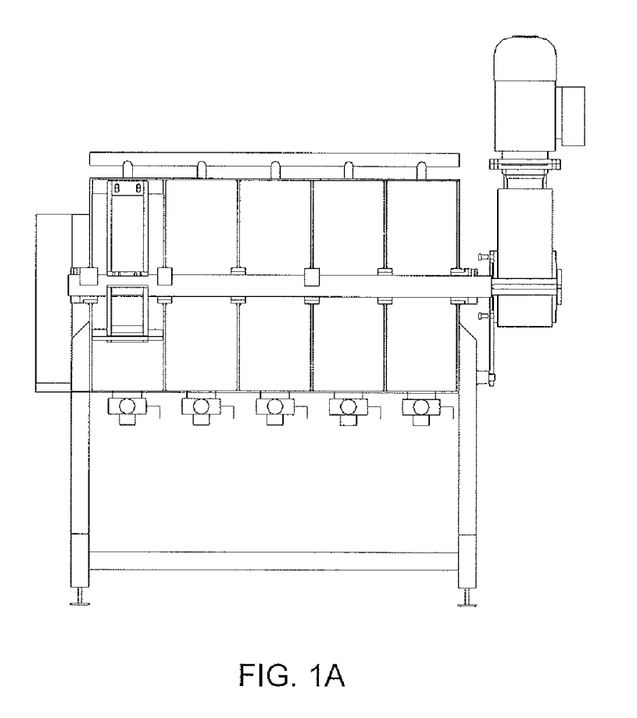
FIG. 1A shows a longitudinal view and FIG. 1B shows a transverse view of a mixer useful for practice of the methods of the invention.
Figure 1B:
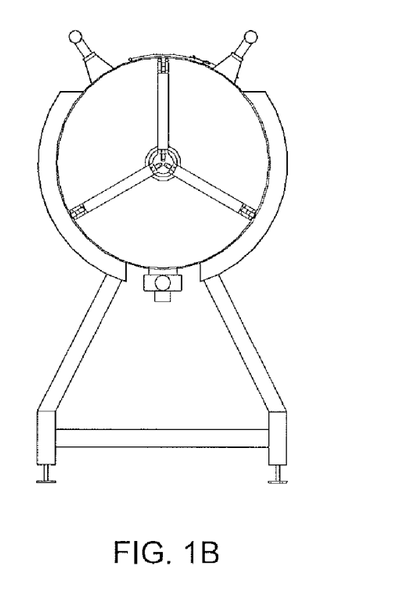

The hydrolysis reactor was designed in order to perform experiments with liquefaction and hydrolysis solid concentrations above 20% DM shown in longitudinal view in FIG. 1A and in transverse view in FIG. 1B. The reactor consisted of a horizontally placed drum divided into 5 separate chambers each 20 cm wide and 60 cm in diameter. A horizontal rotating shaft mounted with three paddlers in each chamber was used for mixing/agitation. A 1.1 kW motor was used as drive and the rotational speed was adjustable within the range of 2.5 and 16.5 rpm. The direction of rotation was programmed to shift twice a minute between clock and anti-clock wise. A water-filled heating jacket on the outside enabled the control of the temperature up to 80° C.

Figure 2:
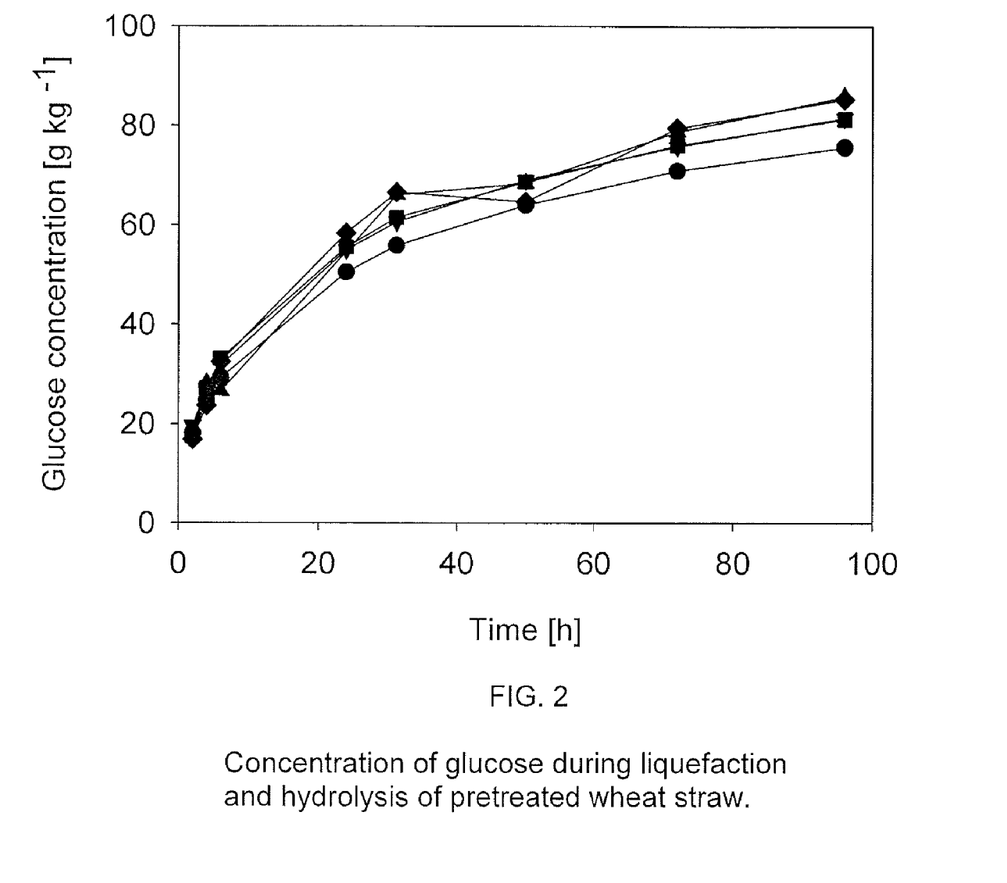
FIG. 2 shows concentration of glucose during liquefaction and hydrolysis of pretreated wheat straw at dry matter content 20% (●), 25% (▼), 30% (■), 35% (♦) and 40% (▲) using an enzyme loading of 7 FPU (g DM)$^{-1}$
Figure 3:
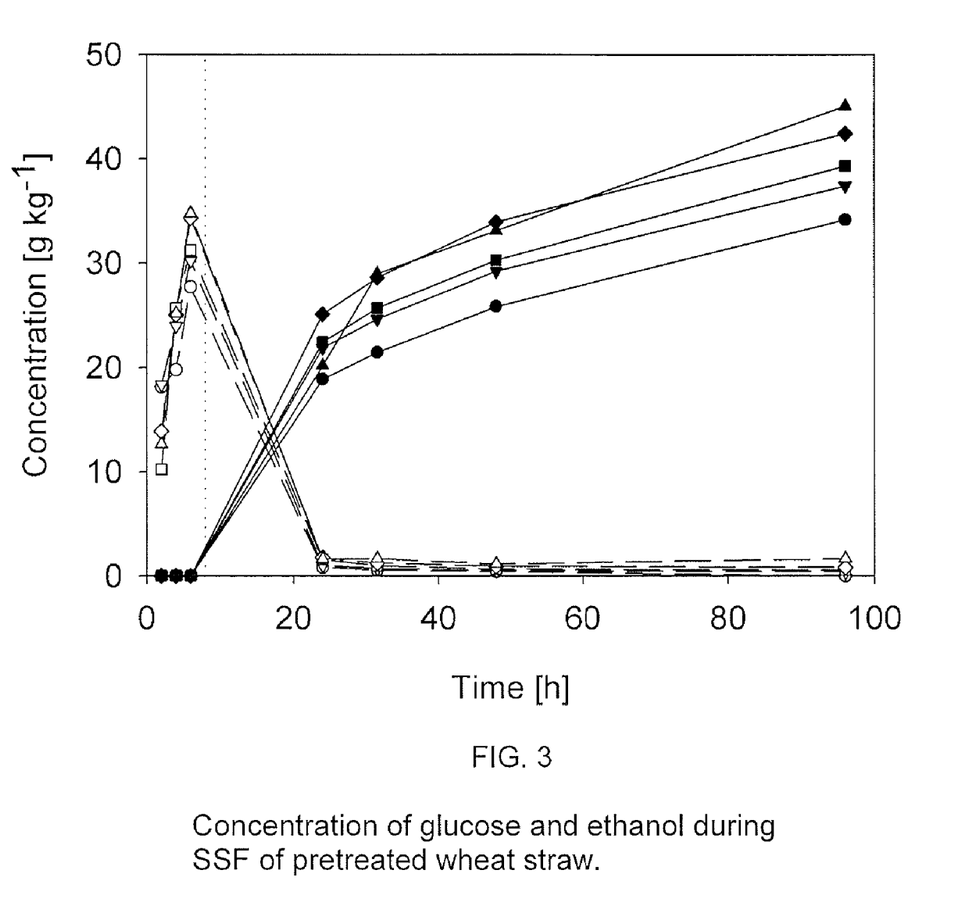
FIG. 3 shows concentration of glucose (open symbols) and ethanol (closed symbols) during liquefaction and hydrolysis of pretreated wheat straw in a simultaneous saccharification and fermentation (SSF) process at dry matter content 20% (●), 25% (▼), 30% (■), 35% (♦) and 40% (▲) using an enzyme loading of 7 FPU (g DM)$^{-1}$. Yeast added after 8 h (dotted line).

The chambers were filled with pressed pretreated wheat straw with an average size of approximately 40 mm (pre-treated by counter-current water extraction at 180-200° C. for 5-10 min. with a water and dry matter flow ratio of 5:1) and water to give an initial DM content of 20 to 40%. CELLUCLAST 1.5 FG L, a liquid cellulase preparation, and NOVOZYM 188, a liquid cellulase preparation enriched in 1,4-β-D-glucosidase, in 5:1 ratio were added to give an enzyme loading of 7 FPU per g DM. The liquefaction and hydrolysis was performed at 50° C. and pH 4.8 to 5.0. The mixing speed was 6.6 rpm. Simultaneous saccharification and fermentation (SSF) experiments were performed by lowering the temperature to 32° C. after 8 h of liquefaction and hydrolysis and following the addition of 15 g of compressed baker's yeast (De Danske Spritfabrikker) per kg of initial DM. Liquefaction and hydrolysis was possible with initial DM content of up to 40% DM (See FIG. 2 and FIG. 3). With initial 40% DM it was possible to reach glucose concentrations of 80 g kg$^{-1}$ after 96 h. It was also possible to operate the process as SSF (See FIG. 3), thereby reducing the product inhibition of the cellulases caused by the glucose accumulation. It was possible to ferment the hydrolysates with up to 40% initial DM content using normal baker's yeast. Under not fully anaerobic conditions the ethanol yield was 80, 79, 76, 73 and 68% of what was theoretically obtainable at 20, 25, 30, 35 and 40% DM, respectively.

EXAMPLE 4

Whole Crop Liquefaction, Saccharification and Fermentation

Lignocellulosic and starch containing biomass can be processed simultaneously using gravity mixing and a mixture of cellulases, hemicellulases and amylases. The lignocellulosic biomasses may be derived from agricultural crops consisting of e.g. corn stover, straw e.g. from rice, wheat, rye, oat, barley, rye, rape and sorghum, tubers e.g. beet, potato, cereals from e.g. rice, wheat, rye, oat, barley, rye, rape, sorghum, wood consisting of softwood e.g. Pinus sylvestris, Pinus radiata, hardwood e.g. Salix spp., Eucalyptus spp., municipal solid waste, waste paper and similar biomasses.

The hydrolysis reactor described in example 3 was used for the experiments. Wheat straw (primarily a lignocellulose source) was pretreated using counter-current water extraction at 180-200° C. for 5-10 min. with a water and dry matter flow ratio of 5:1. Wheat grain (primarily a starch source) was dry milled using a Kongskilde roller mill. The wheat grain and pretreated straw with an average size of approximately 40 mm was mixed in a 1:1 ratio on a dry basis. DM was adjusted to between 30 and 40% by addition of water. CELLUCLAST 1.5 FG L, a liquid cellulase preparation, and NOVOZYM 188, a liquid cellulase preparation enriched in 1,4-β-D-glucosidase, in a 5:1 ratio were added to give an enzyme loading of 7 FPU per g DM of straw. Hydrolysis of starch was carried out using cold mash enzyme NS50033 (Novozymes A/S, Bagsvaerd, Denmark) at a loading of 3.5 g per kg of wheat grain. The liquefaction and hydrolysis was performed at 50° C. and pH 4.8 to 5.0. After 8 h, the temperature was lowered to 34° C. and 15 g of compressed baker's yeast (De Danske Spritfabrikker) was added per kg of initial DM. An experiment with straw only at 30% DM was run in parallel.

Figure 4:
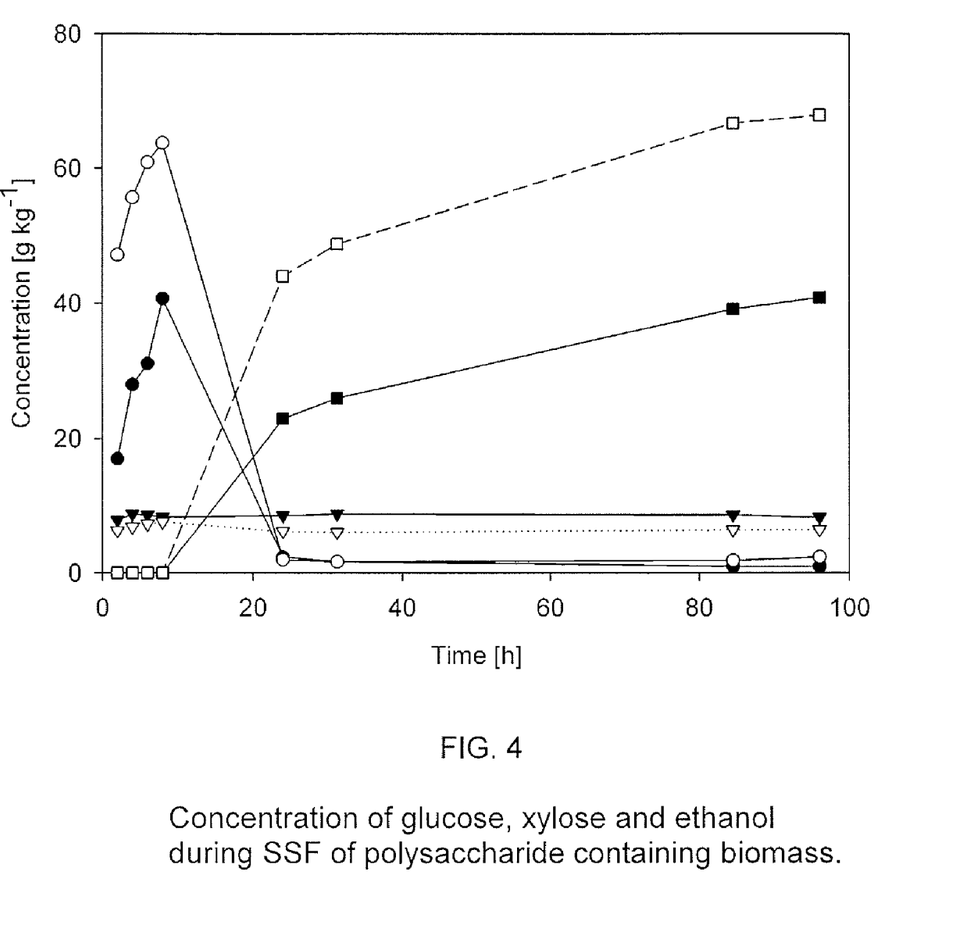
FIG. 4 shows concentration of glucose (●), xylose (▼) and ethanol (■) during liquefaction and hydrolysis of pretreated wheat straw (closed symbols) and a mixture of pretreated wheat straw and wheat grain (open symbols) in a simultaneous saccharification and fermentation (SSF) process. Yeast was added after 8 h of liquefaction and hydrolysis.

Mixing straw with grain resulted in a fast initial accumulation of glucose in the liquefaction and hydrolysis step compared to applying straw only (FIG. 4). After 96 h of liquefaction and SSF the ethanol concentration was 41 g kg$^{-1}$ using only wheat straw as the only substrate (See FIG. 4). In the experiment with straw and grain the ethanol concentration reached 68 g kg$^{-1}$.

EXAMPLE 5

Low Temperature Liquefaction of Starch or Starch Containing Materials

A process according to the present invention can also be applied for low temperature processing of refined starch or starch containing materials (e.g. beet, potato, cereals from e.g. rice, wheat, rye, oat, barley, rye, sorghum). According to example 4, heat pre-treatment of the grain is not necessary for liquefaction and hydrolysis of starch. Dry milling is on the other hand generally used for pre-treatment of starch containing grains. Dry milled grains with a dry matter content of 20-60% are loaded into the gravity mixer. Cold mash enzyme NS50033 (Novozymes A/S, Bagsvaerd, Denmark) or alpha-amylase and glucoamylases are added simultaneously. A full liquefaction and saccharification of the starch is then possible in a one-pot process. Temperature and pH ranges during the enzymatic hydrolysis process are defined by the enzymes and will be in the range of 25-60° C., preferably 40-55° C., and pH 3-12, preferably pH 3-8, respectively.

The process may be combined with SSF.

CITED LITERATURE

Galbe, M., Zacchi, G. (2002). A review of the production of ethanol from softwood. Appl. Microbiol. Biotechnol. 59:618-628.

Giovannozzi-Sermanni, G., D'Annibale, A., Perani, C., Porri, A., Falesiedi, G. (2002). Solid-state bioreactors for the sustainability. http://www.unitus. itdipartimenti/dabac/progetti/ssbioreactors/solidstatebioreactor.htm Gregg, D., Saddler, J. N. (1995). Bioconversion of lignocellulosic residues to ethanol: Process flow-sheet development. Biomass Bioenerg. 9:287-302.

Mais, U., Esteghalalian, A. R., Saddler, J. N. (2002). Influence of mixing regime on enzymatic saccharification of steam-exploded softwood chips. Appl. Biochem. Biotechnol. 98-100:463-472.

U.S. Pat. No. 4,409,329
US2002117167A
US2004005674A

The invention claimed is:

1. A process for treating polysaccharide containing biomasses characterized by subjecting a polysaccharide containing biomass having a final dry matter content of above 20% and comprising lignocellulosic biomass to:
    a) enzymatic hydrolysis using at least one cellulase enzyme, and
    b) mixing by a free fall type mixing that provides mechanical degradation of the biomass during hydrolysis,
    wherein the mixed biomass is liquefied to a liquid without any or with only a few remaining large fibres and particles in the process.

2. A process for treating polysaccharide containing biomasses characterized by subjecting a polysaccharide containing biomass having a final dry matter content of above 20% and comprising lignocellulosic biomass to:
    a) enzymatic hydrolysis using at least one cellulase enzyme, and
    b) mixing by a free fall type mixing that provides mechanical degradation of the biomass during hydrolysis,
    wherein the biomass comprises a lignocellulosic biomass having a distribution of particle sizes in which at least 20% (w/w) are between 26-70 mm in size before pre-treatment, and
    wherein the mixed biomass is liquefied to a liquid without any or with only a few remaining large fibres and particles in the process.

3. A process for treating polysaccharide containing biomasses characterized by subjecting a polysaccharide containing biomass having a final dry matter content of above 20% and comprising lignocellulosic biomass to:
    a) enzymatic hydrolysis using at least one cellulase enzyme, and
    b) mixing by a free fall type mixing that provides mechanical degradation of the biomass during hydrolysis,
    wherein the mixed biomass is liquefied to a liquid without any or with only a few remaining large fibres and particles in the process within 3 to 24 hours.

4. A process according to claim 1, wherein the polysaccharide containing biomass comprising lignocellulosic biomass is further characterized by comprising primarily a mixture of starch containing grains or refined starch and lignocellulosic biomasses derived from agricultural crops.

5. A process according to claim 2, wherein the polysaccharide containing biomass comprising lignocellulosic biomass is further characterized by comprising primarily a mixture of starch containing grains or refined starch and lignocellulosic biomasses derived from agricultural crops.

6. A process according to claim 1, wherein the polysaccharide containing biomass comprises primarily lignocellulosic biomass derived from corn stover, bagasse, rice straw, wheat straw, rye straw, oat straw, barley straw, rye straw, rape straw, sorghum straw, softwood, hardwood, municipal solid waste, or waste paper.

7. A process according to claim 2, wherein the polysaccharide containing biomass comprises primarily lignocellulosic biomass derived from corn stover, bagasse, rice straw, wheat straw, rye straw, oat straw, barley straw, rye straw, rape straw, sorghum straw, softwood, hardwood, municipal solid waste, or waste paper.

8. A process according to claim 3, wherein the polysaccharide containing biomass comprises primarily lignocellulosic biomass derived from corn stover, bagasse, rice straw, wheat straw, rye straw, oat straw, barley straw, rye straw, rape straw, sorghum straw, softwood, hardwood, municipal solid waste, or waste paper.

9. A process according to claim 1 wherein the polysaccharide containing biomass comprises primarily lignocellulosic biomass that has been subjected to heat pre-treatment between 110-250° C.

10. A process according to claim 2 wherein free fall mixing is provided by a drum mixer, a mixer with a rotary axis lifting the biomass, a mixer with a horizontal placed stirrer shaft lifting the biomass, or similar mixer.

11. A process according to claim 3 wherein free fall mixing is provided by a drum mixer, a mixer with a rotary axis lifting the biomass, a mixer with a horizontal placed stirrer shaft lifting the biomass, or similar mixer.

12. A process according to claim 1 carried out as a continuous, fed-batch, or other semi-continuous process.

13. A process according to claim 2 carried out as a continuous, fed-batch, or other semi-continuous process.

14. A process according to claim 3 carried out as a continuous, fed-batch, or other semi-continuous process.

15. A process according to claim 1 wherein additional mechanical degradation of the biomass is provided by steel balls or similar material that collides with the biomass during mixing.

16. A process according to claim 2 wherein additional mechanical degradation of the biomass is provided by steel balls or similar material that collides with the biomass during mixing.

17. A process according to claim 3 wherein additional mechanical degradation of the biomass is provided by steel balls or similar material that collides with the biomass during mixing.

18. A process according to claim 1 wherein the mixed biomass is liquefied to a liquid without any or with only a few remaining large fibres and particles in the process within 3 to 24 hours.

19. A process according to claim 2 wherein the mixed biomass is liquefied to a liquid without any or with only a few remaining large fibres and particles in the process within 3 to 24 hours.

20. A process according to claim 3, wherein the polysaccharide containing biomass comprising lignocellulosic biomass is further characterized by comprising primarily a mixture of starch containing grains or refined starch and lignocellulosic biomasses derived from agricultural crops.

* * * * *